United States Patent [19]

Sukman

[11] 4,264,593
[45] Apr. 28, 1981

[54] TRIS(ARYL)ALKYL PHOSPHONIUM HALIDES AND PESTICIDAL COMPOSITIONS THEREOF

[75] Inventor: Edwin L. Sukman, Montclair, N.J.

[73] Assignee: M&T Chemicals, Inc., Woodbridge, N.J.

[21] Appl. No.: 90,080

[22] Filed: Oct. 31, 1979

[51] Int. Cl.³ .......................... A01N 57/22; C07F 9/54
[52] U.S. Cl. .......................................... 424/198; 568/9
[58] Field of Search .................. 260/606.5 F; 424/198

[56] References Cited

U.S. PATENT DOCUMENTS 3,642,989  2/1972  Martin et al. ..................... 424/198 X Primary Examiner—Richard Raymond
Attorney, Agent, or Firm—Stanley A. Marcus; Robert Spector

[57] ABSTRACT

Tri(phenyl)alkyl phosphonium halides wherein the phenyl groups contain a long chain or sterically hindered alkyl group are novel and exhibit efficacious levels of fungicidal and bacteriocidal activity. The presence of the alkyl substituent eliminates or significantly reduces the phytotoxicity that characterizes the corresponding unsubstituted phosphonium compounds.

8 Claims, No Drawings

TRIS(ARYL)ALKYL PHOSPHONIUM HALIDES AND PESTICIDAL COMPOSITIONS THEREOF

BACKGROUND OF THE INVENTION

This invention relates to novel tris(aryl)alkyl phosphonium compounds and to the use of these compounds as bacteriocides and non-phytotoxic fungicides.

The prior art teaches that many quaternary phosphonium compounds exhibit useful levels of insecticidal, fungicidal and bacteriocidal activity. Specific patents relating to this subject include U.S. Pat. Nos. 3,230,068; 2,946,824; 2,418,652 and 3,445,570. Unfortunately many of the phosphonium compounds disclosed in the prior art, particularly tri(phenyl)alkyl phosphonium halides, are moderately to severely phytotoxic when employed at the minimum concentration level required to control fungi such as bean mildew on a living plant. These compounds therefore cannot be used as agricultural pesticides.

It has now been found that the phytotoxicity of tri(phenyl)alkyl phosphonium compounds can be reduced to a non-detrimental level or eliminated entirely without significantly affecting fungicidal and bacteriocidal activity if certain substituents are present on the phenyl groups.

SUMMARY OF THE INVENTION

This invention provides novel tris(p-hydrocarbylphenyl) alkyl phosphonium halides of the general formula

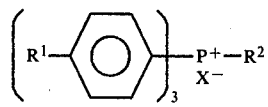

wherein $R^1$ is selected from the group consisting of alkyl containing from 6 to 12 carbon atoms, $(CH_3)_3C-$,

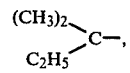

cyclohexyl or phenyl, $R^2$ represents an alkyl group containing from 1 to 4 carbon atoms and X is chlorine, bromine or iodine.

This invention also provides non-phytotoxic fungicidal compositions suitable for combatting fungi on living plants. These compositions comprise a liquid or solid carrier and a fungicidally effective amount of one of the present tris(p-alkylphenyl)alkyl phosphonium halides.

The present compounds can be employed as the active ingredient in bacteriocidal compositions that are effective against both gram positive and gram negative bacteria.

DETAILED DESCRIPTION OF THE INVENTION

The phosphonium halides of the present invention are novel by virtue of the alkyl group located in the para position of the phenyl group relative to the phosphorus atom. These compounds can be prepared by reacting the corresponding phosphine, represented by the formula

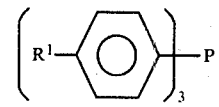

with an alkyl halide of the formula $R^2X$. The terms $R^1$, $R^2$ L and X have been previously defined. If the desired phosphine is not available, it can be synthesized using any of the known methods for preparing phosphines. A preferred method employs the reaction of an organomagnesium halide.

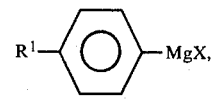

with a phosphorus trihalide. The preparation of several preferred compounds is described in the accompanying examples.

The compounds of this invention are particularly useful as fungicides. Unlike other tri(phenyl)alkyl phosphonium compounds, the present compounds are substantially non-phytotoxic, which makes it possible to employ these compounds to control fungus diseases such as bean mildew, bean rust and leaf spot of rice on agricultural crops without damaging the host plants. This surprisingly low level of phytotoxicity is attributed to the presence of a relatively long alkyl group containing from 6 to 12 carbons, a branched alkyl group containing from 3 to 5 carbon atoms, or a phenyl or cyclohexyl ring structure on the phenyl group that is bonded to the phosphorus atom.

The following examples disclose the general method for preparing phosphonium halides as applied to some of the preferred compounds of this invention. The examples also demonstrate the unique combination of excellent fungicidal and bacteriocidal activity and low phytotoxicity that characterizes the present compounds. All parts and percentages are by weight unless otherwise specified.

EXAMPLE 1

General Preparative Method

The procedure for preparing methyl tris(p-t-amylphenyl) phosphonium bromide typifies the general procedure employed to prepare the compounds of this invention.

A. p-Bromo-t-amylbenzene

A glass reactor equipped with a mechanically driven stirrer, addition funnel and hydrogen bromide trap was charged with 300 g (2.02 mole) of t-amylbenzene and 8 g of iron filings. Bromine (374 g, 2.02 mole) was added dropwise at a rate such that the temperature of the reaction mixture was maintained at about 35° C. The reaction mixture was stirred for 15 hours while being heated to a temperature of 50° C. The contents of the reactor were then cooled and combined with 200 cc of a saturated aqueous sodium bisulfite solution. After being stirred for a few moments the reaction mixture was filtered. The organic layer was then separated and combined with a quantity of anhydrous magnesium sulfate to remove any water present. The liquid phase was then separated and distilled under a pressure of 0.1 mm of mercury. The fraction boiling from 70° to 75° C.

was collected and analyzed for carbon, hydrogen and bromine.

|   | Calculated | Found |
|---|---|---|
| C | 58.2 | 58.5 |
| H | 6.61 | 6.56 |
| Br | 35.2 | 33.2 |

The distillate weighed 430 g (94% yield) and exhibited an index of refraction ($n_D^{20}$) of 1.5380.

B. Tris(p-t-amylphenyl) phosphine

A glass reactor equipped with a water-cooled reflux condenser, addition funnel, mechanically driven stirrer, thermometer and a nitrogen inlet was charged with 37 g (1.55 mole) of magnesium chips. A 30 cc portion of a solution containing 340.5 g (1.5 mole) of p-bromo-t-amylbenzene and one liter of tetrahydrofuran was added from the addition funnel with rapid stirring. When the reaction initiated, as indicated by an increase in the temperature of the reaction mixture, the remainder of the solution was added at a rate which maintained the reaction mixture at the boiling point without external heating. Following completion of the addition the reaction mixture was heated at the boiling point for two hours and allowed to cool to 15° C. A solution containing 68.8 g (0.5 mole) of phosphorus trichloride was then added at a rate which maintained the temperature of the reaction mixture at from 15° to 25° C. Following completion of the addition the reaction mixture was heated to the boiling point for two hours, allowed to cool and then poured with stirring into a mixture containing one liter of ice and 100 cc of concentrated aqueous hydrochloric acid. Stirring was continued until all of the ice melted, at which time sodium carbonate was gradually added until the pH of the solution was 7. One liter each of chloroform and water was added, the organic layer was separated and the water in this phase was removed using anhydrous magnesium sulfate. The chloroform was then removed by evaporation under the reduced pressure produced by a water aspirator to yield a yellow solid. This material was combined with a portion of methanol, pulverized and mixed thoroughly for one hour. The dried solid material weighed 170 g (72% yield), melted from 129.5° to 130° C. and was found to contain 83.3% carbon, 9.34% hydrogen and 6.50% phosphorus. The calculated values for the expected product are 83.9% carbon, 9.53% hydrogen and 6.57% phosphorus.

C. Methyl tris(p-t-amylphenyl)phosphonium Bromide

A mixture containing 28.3 g (0.06 mole) of tris(p-t-amylphenyl)phosphine, 28.5 g (0.3 mole) of methyl bromide and 200 cc of benzene was prepared and stored at ambient temperature for 24 hours. The solvent was then removed under reduced pressure and the solid residue was stirred together with a quantity of diethyl ether for one hour. The recovered solid material weighed 33 g (97% yield) after drying and was found to contain 71.3% carbon, 8.44% hydrogen, 5.15% phosphorus and 14.0% bromine. The calculated values for the expected compound are 72.0% carbon, 8.47% hydrogen, 5.47% phosphorus and 14.1% bromine.

EXAMPLE 2

A number of methyl tris(p-substituted phenyl) phosphonium halides were prepared using the general procedure described in the preceding Example 1. These compounds together with their melting ranges and analytical data are summarized in the following table. The compounds are represented by the general formula $$\left[ R^1 - \left\langle \bigcirc \right\rangle - \right]_3 \overset{+}{\underset{R^2}{P}} X^-$$

| | | | | Analysis | | | |
|---|---|---|---|---|---|---|---|
| | | | | Calculated | | Found | |
| $R^1$ | $R^2$ | X | M.R. (°C.) | P | X | P | X |
| t-butyl | CH$_3$ | Br | 129–133 | 4.75 | 15.2 | 5.47 | 15.6 |
| cyclohexyl | CH$_3$ | Br | 184–188 | 5.14 | 13.3 | 5.19 | 12.9 |
| phenyl | CH$_3$ | Br | 118–125 | 5.30 | 13.7 | 5.07 | 10.9 |
| n-hexyl | CH$_3$ | Br | viscous liquid | 5.09 | 13.1 | 5.19 | 11.1 |
| dodecyl | CH$_3$ | Br | viscous liquid | 3.60 | 9.29 | 3.50 | 8.47 |
| isopropyl | CH$_3$ | Br | 105–190 | 6.41 | 16.5 | 6.39 | 16.1 |
| phenyl | CH$_3$ | I | 130 | 4.90 | 20.1 | 4.50 | 19.0 |
| t-butyl | CH$_2$CN | Cl | 197–200 | 6.13 | 6.13 | 6.21 | 7.07 |

The novel compounds of the foregoing examples can be applied to soil or plants by a variety of means. Compositions suitable for application to soil or plants include liquid extending agents such as solvents or diluents within which the novel active compounds of this invention are dissolved or suspended, wetting or emulsifying agents which assist in the uniform dispersing in water of solutions containing the active ingredient and a water-immiscible solvent and, optionally, an adhesive or spreading agent which improves the contact of the present compounds with soil and plant surfaces or other surfaces to be protected.

The present compounds need not be dissolved in the extending agent, but may be merely dispersed or suspended in the extending agent as a suspension or emulsion. The compounds may first be dissolved in a suitable organic solvent and the organic solution of the active ingredient then incorporated in water or in an aqueous extending agent in the form of a heterogeneous dispersion. Examples of some suitable organic solvent for use as extending agent include hexane, benzene, toluene, acetone, cyclohexanone, methyl ethyl ketone, isopropanol, butanediol, methanol, diacetone alcohol, xylene, dioxane, isopropyl, ether, ethylene dichloride, tetrachlorethane, hydrogenated naphthalene, solvent naphtha and petroleum fractions, such as kerosene.

Solid extending agents in the form of particulate solids are very useful in the practice of this invention. In using this type of extending agent, the active ingredient is either absorbed or dispersed on or in a finely-divided solid material. Preferably, the solid extending agents are not hygroscopic, but are materials which render the compositions permanently dry and free-flowing. Suitable solid extending agents include the natural clays such as china clays, the bentonites, and attapulgites; other minerals such as talc, pyrophyllite, quartz, diatomaceous earth, fuller's earth, chalk, rock phosphate, kaolin, kiselguhr, volcanic ash, salt; chemically modified minerals such as acid-washed bentonite, precipitated calcium phosphate, calcium carbonate, calcined magnesia, colloidal silica, and other solid materials such as powdered cork, powdered wood and powdered pecan or walnut shells. These materials are used in finely divided form, of approximately a size range passing through 20 to 40 mesh screen. Particulate solid concentrates of compositions are applied to the soil by admixture at the time of application with a particulate solid carrier material.

If desired, the compounds of this invention can be applied as a wettable powder using water as the liquid carrier material. When using this method, a wetting agent or surface active agent is added to a solid concentrate composition to render the particulate solid extending agent wettable by water and thereby obtain a stable aqueous dispersion or suspension suitable for use as a spray. The extending agents employed for wettable powders are very finely divided with an average particle size of 100 mesh or less. Surface active agents suitable for wetting, emulsifying or dispersing the present compounds are either liquid or solid and can be of the anionic, cationic, or non-ionic type. Suitable surface active agents are the organic types and include conventional soaps, such as the water-soluble salts of long chain carboxylic acids; the amino soaps, such as the amine salts of long-chain carboxylic acids; the sulfonated animal, vegetable and mineral oils; quaternary salts of high molecular weight acids; rosin soaps, such as salts of abietic acid; sulfuric acid salts of high molecular weight organic compounds; algin soaps; ethylene oxide condensed with fatty acids, alkyl phenols and mercaptans; and other simple and polymeric compositions having both hydrophillic and hydrophobic functions.

Concentrated compositions containing the compounds of this invention should have the compound and the surface active agent present in higher concentrations than the toxicant compositions applied in the field so that upon dilution with a solid or liquid carrier the resultant compositions will contain optimum proportions of the active novel compounds and surface active agent.

The use of a surface active agent may be necessary in formulating a liquid concentrate composition to obtain a sufficiently high concentration of the toxicant. The liquid extending agent must be selected not only on the basis of the desired concentration of toxicant but also upon the basis of the solution temperature of the total composition. Thus, in some formulations, a particular combination of solvents gives us sufficiently low solution temperatures but the amount of toxicant dissolved or dispersed in the mixture is insufficient and a suitable surface active agent must be selected such that the novel compound can be uniformly dispersed in the composition. Preferably a concentrate composition has a solution temperature below 0° C., although compositions having higher solution temperatures can be used.

The concentration of the present phosphonium compounds in a particulate solid or dust concentrate composition may vary over wide ranges depending upon the nature of the solid extending agent. It is to be noted that the surface active agents are not usually required in dust concentrate compositions, although they can be used if desired. If a dust concentrate compsition is to be applied as a wettable powder, a surface active agent should be present in the concentrate composition. Ordinarily, the concentration of surface activate agent will be from 0.1 to 15% by weight of the composition.

The carrier or extending material used to achieve uniform distribution of the present compounds when employed as pesticides may be either a liquid or a particulate solid. The liquid and solid extending agents used to prepare concentrate compositions can also be used as the carrier, however, the use of these extending agents may not be economical. Water is the preferred liquid carrier for both liquid and wettable powder concentrates. Suitable particulate solid carriers include the particulate extending agents noted above as well as solid fertilizers, such as ammonium nitrate, urea and super phosphate, as well as other materials in which plants can take root and grow such as compost, sand, and humus. Liquid and dust concentrate compositions containing the novel compound of this invention can also contain other additaments such as fertilizer and pesticides. These additaments may be used as, or in combination with the carrier materials.

Compositions containing the present compounds can be applied to plants in any conventional manner. Thus, dust and liquid compositions can be applied to the foliage of growing plants by use of spray dusters. Solid compositions containing the novel compounds of this invention can be applied from airplanes as a dust.

EXAMPLE 3

This example demonstrates the unique combination of excellent fungicidal activity and low phytotoxicity exhibited by the present phosphonium halides.

TESTING PROCEDURE

1. General

The phosphonium halides were formulated into sprayable compositions by first dissolving or dispersing them in a 90/10 weight ratio mixture of water/acetone containing a non-ionic surfactant. The resultant stock solutions or dispersions were diluted with a water-surfactant mixture to obtain the desired concentration of tin compound while maintaining the surfactant concentration at 100 parts per million(ppm.). Samples which proved difficult to emulsify were homogenized using a colloid mill or tissue homogenizer.

2. Evaluation of effectiveness of phosphonium halides against plant fungi and weeds.

The efficacy of several compounds of this invention as fungicides and herbicides was evaluated against three different species of fungi and six weeds.

Fungi: Bean powdery mildew, bean rust and leaf spot of rice (helminthosporium);
Weeds: Morning Glory, Zinnia, Mustard, Fox Millet, Crabgrass and Barnyard Grass.

3. SPECIFIC EVALUATION PROCEDURES

A. Bean Powdery Mildew

Tender green bean plants with fully expanded primary leaves are innoculated with spores of the powdery mildew fungus (erysiphe polygoni) 48 hours prior to applications of test chemicals. Chemicals are applied at the concentrations indicated in the following tables by placing the plants on a revolving turntable and spraying them with the test chemical formulation. When the spray deposit dries, the plants are placed in a greenhouse for between 7 and 10 days, at which time the amount of mildew on the primary leaves is rated. Plants not treated with any fungicide serve as controls.

B. Bean Rust

Pinto bean plants with fully expanded primary leaves are innoculated with spores of the bean rust fungus (uromyces phaseoli) and incubated for 24 L hours. Test chemicals are then applied and the plants evaluated using the procedure specified for bean powdery mildew.

C. Leaf Spot of Rice (helminthosporium)

Rice plants are sprayed with formulations containing the test compound. As soon as the spray has dried, the plants are innoculated with a spore suspension of helminthosporium and placed in an incubation chamber for 24 hours, after which they are removed and held until lesions have developed. Plants not treated with any fungicide serve as controls.

D. Herbicidal Activity

The plants are sprayed with formulations of the phosphonium compounds when the first true leaves have appeared. The responses are rated 12 to 16 days after treatment, and the results are summarized in the table. The concentration of phosphonium compound is expressed in pounds per acre, and appears in parenthesis below the efficacy rating, expressed as degree of plant injury. The rating is a composite one and is obtained by totaling the individual ratings for the six plants tested.

40–60 = severe phytotoxicity
20–40 = moderate phytotoxicity
0–20 = no or slight phytotoxcity All of the phosphonium compounds tested, including the ten control compounds, exhibited significant fungicidal activity. In addition, the present compounds, which contain sterically large alkyl substituents on the phenyl group, exhibited no phytotoxicity and low or no herbicidal activity.

excellent control is obtained on gram positive and gram negative bacteria in addition to mildew organisms.

A. Testing

The candidate compounds were tested by the broth dilution technique to determine the minimum inhibitory concentration (M.I.C.) for three species, *S. aureus* (gram +), *P. aeruginosa* (gram −), and *A. niger* (wood fungus). Preliminary dilutions were in ethanol to give a concentration tenfold higher than the dilution in each series. This concentration was then used to prepare the final dilutions in nutrient broth. Three sets of broth tubes were prepared for each compound. Each set was innoculated with *S. aureus, P. aeruginosa* and a spore suspension of *A. niger,* respectively. The tubes were examined after being incubated for 48 hours at 35° C. for *S. aureus* and *P. aeruginosa* of for 2 weeks at room temperature for *A. niger.* As the phenyl ring substituents increase in size from H to $CH_3$ to bulky group substitution, the control on gram negative and mildew becomes evident. In addition, the control of gram positive bacteria is enhanced.

Bacteriocidal Activity of Methyltriaryl Phosphonium Compounds

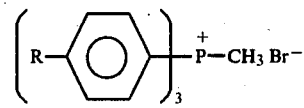

Fungicide and Herbicide Activity of Triarylalkyl-Phosphonium Halides:

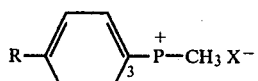

| | | Fungicide (Concentration in ppm) | | | | | | | | | | | Post Emergence Herbicide - Composite of 6 Rate (lbs/acre) ratings | | | |
|---|---|---|---|---|---|---|---|---|---|---|---|---|---|---|---|---|
| | | Bean Mildew 7 Days | | | Bean Rust | | | | Leaf Spot of Rice | | | | | | | |
| R | X | 250 | 125 | 62 | 250 | 125 | 62 | 31 | 250 | 125 | 62 | 31 | 10 | 5 | 2.5 | 1.2 |
| $(CH_3)_3C-$ | Br | 9 | — | — | 10 | 10 | 10 | 10 | 9 | 8 | 7.5 | 9 | 14 | — | — | — |
| $CH_3CH_2C(CH_3)(CH_3)-$ | Br | 8 | — | — | 10 | 10 | 10 | 10 | 9 | 9.5 | 9 | 9 | 6 | — | — | — |
| (S-thienyl) | Br | 9 | 7 | 7.5 | 10 | 10 | 10 | 10 | 9 | 10 | 10 | 9 | 0 | — | — | — |
| (phenyl) | Br | 7 | — | — | 9 | 9 | 9 | 8.5 | 8.5 | 9 | 9 | 9 | 0 | — | — | — |
| CONTROL COMPOUNDS | | | | | | | | | | | | | | | | |
| H | Cl | 0 | — | — | 5.5 | — | — | — | 5 | — | — | — | 23 | — | — | — |
| H | Br | 2.5 | — | — | 5.5 | 7 | 6 | 5 | 5 | — | — | — | 25 | 25 | 14 | — |
| H | I | 3* | — | — | * | — | — | — | 3 | — | — | — | 29 | 31 | 24 | — |
| $CH_3$ | Cl | 6 | — | — | * | 9* | 9 | 8.5 | 5* | — | — | — | 41 | 42 | 32 | 15 |
| $CH_3$ | Br | 9* | 5* | 2* | 9* | 9* | 9 | 8.5 | 9 | 4 | 4* | 4 | 51 | 35 | 34 | 23 |
| $CH_3$ | I | 10* | 7* | 7* | — | — | — | — | 8* | 10* | 6* | 3* | 41 | 43 | 24 | 15 |
| $CH_3O$ | Br | 4* | — | — | 7 | 6 | 6.5 | 5.5 | 5 | — | — | — | 35 | 13 | 19 | 18 |
| Cl | Br | 4.5 | — | — | 6* | — | — | — | 7 | — | — | — | 14 | — | — | — |
| $C_2H_5$ | Br | 9.5 | 9.5 | 9 | 10* | 10* | 10 | 10 | 4 | — | — | — | 40 | 34 | 21 | 9 |
| $(CH_3)_2C-H$ | Br | 7.5 | — | — | 10* | — | — | — | 3* | — | — | — | 34 | 29 | 21 | 15 |

* = Significant level of phytotoxicity observed

4. Bacteriocide Tests

Most bacteriocidal materials control gram positive bacteria, but do not control gram negative species. This includes many of the known antibiotics and phosphonium salts. When triarylphosphonium halides are substituted with bulky alkyl groups on the phenyl group

| R | Minimum Effective Concentration (PPM) For Inhibition Of | | |
|---|---|---|---|
| | S. Aureus | P. Aeruginosa | A. Niger |
| $(CH_3)_2C(C_2H_5)-$ | 0.18 | 8 | 2 |

-continued
Bacteriocidal Activity of Methyltriaryl Phosphonium Compounds

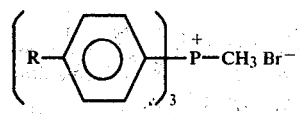

| R | Minimum Effective Concentration (PPM) For Inhibition Of | | |
|---|---|---|---|
|  | S. Aureus | P. Aeruginosa | A. Niger |
| [S-thienyl] | 0.18 | 16 | 2.5 |
| $(CH_3)_3C-$ | 0.18 | 32 | 4 |
| $CH_3CH_2-$ (control) | 4 | N.T. | 32 |
| $CH_3-$ (control) | 7.5 | >1000 | 250 |

N.T. = not tested

EXAMPLE 4

This example demonstrates that the present phosphonium halides, which contain sterically hindered substituents, are more effective with regard to imparting resistance to mildew to cotton fabric than a quaternary ammonium compound conventionally employed for this purpose.

TEST METHOD

Fabric Treatment

The compounds tested were (1) an alkyldimethylbenzylammonium chloride; (2) hexadecyltriphenylphosphonium bromide. Solutions of 0.05% were made up in distilled water. Strips of cotton 25 mm×75 mm were dipped into the solution and then drained. The wet pickup was from 92–103%. The strips were then air dried and submitted for testing at Gibralter Biological Laboratories, Fairfield, N.J.

Mildew Resistance Test

The samples were designated as follows:

| 1–5 | 1a | alkyltrimethylbenzylammonium chloride |
| 6–10 | 1b | alkyltrimethylbenzylammonium chloride |
| 11–15 | 2a | hexadecyltriphenylphosphonium bromide |
| 16–20 | 2b | hexadecyltriphenylphosphonium bromide |
| 21–25 | 3a | methyl-tris(p-t-amylphenyl)phosphonium bromide |
| 26–30 | 3b | methyl-tris(p-t-amylphenyl)phosphonium bromide |
| 30–40 | control | no additive |

The above samples were soaked for about 3 minutes in an aqueous nutrient solution containing 1% glycerol, 0.1% potassium hydrogen phosphate, 0.1% ammonium nitrate, 0.05% magnesium sulfate and 0.05% yeast autolysate. The pH of the nutrient medium was 5.3. The samples were then allowed to air dry at ambient temperature.

Spore suspensions of A. niger and Penicillium sp. were grown for ten days at room temperature. Spores were harvested with a solution of 0.1% of a surfactant, octyl phenoxy polyethyoxy ethanol, in normal saline. Equal volumes of both species were combined for innoculum. The innoculation was done by hanging the nutrient-treated strips from hooks attached to jar tops and spraying with the spore suspension from a Devilbiss atomizer. The innoculated strips were suspended in 0.3 liter jars containing 50 cc of water and incubated at room temperature for 4 weeks. Observations were recorded each week. The sample were rated according to the following scale:

| 0 | No growth detected |
| + | Growth covering up to 25% of surface |
| ++ | Growth covering 25–50% of surface |
| +++ | Growth covering 50–75% of surface |
| ++++ | Growth covering 75–100% of surface |

The data summarized in the following table clearly indicate the superiority of the subject compounds as fabric mildewcides over known materials such as alkyl dimethylbenzylammonium salts and long-chain alkyltriphenylphosphonium salts, which are related to the compounds of the present invention. The presence of a bulky alkyl substituent on the phenyl groups confers unexpected useful activity on the molecule.

TABLE VIII
RESULTS OF FABRIC TREATMENT TESTS

| Sample No. | | Result | Sample No. | | Result |
|---|---|---|---|---|---|
| 1 | 1a | + | 21 | 3a | + |
| 2 | 1a | ++++ | 22 | 3a | + |
| 3 | 1a | ++++ | 23 | 3a | + |
| 4 | 1a | ++++ | 24 | 3a | + |
| 5 | 1a | ++++ | 25 | 3a | 0 |
| 6 | 1b | ++ | 26 | 3b | + |
| 7 | 1b | ++++ | 27 | 3b | 0 |
| 8 | 1b | ++++ | 28 | 3b | 0 |
| 9 | 1b | ++++ | 29 | 3b | + |
| 10 | 1b | ++++ | 30 | 3b | discarded |
| 11 | 2a | + | 31 | control | ++++ |
| 12 | 2a | + | 32 | " | ++ |
| 13 | 2a | + | 33 | " | ++++ |
| 14 | 2a | + | 34 | " | ++ |
| 15 | 2a | ++ | 35 | " | 0 |
| 16 | 2b | ++ | 36 | " | ++ |
| 17 | 2b | ++ | 37 | " | + |
| 18 | 2b | ++ | 38 | " | ++++ |
| 19 | 2b | + | 39 | " | ++ |
| 20 | 2b | ++ | 40 | " | +++ |

What is claimed is:

1. A tris(p-hydrocarbylphenyl) alkyl phosphonium halide of the general formula

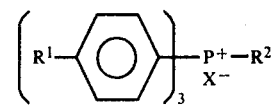

wherein $R^1$ represents an alkyl group containing from 6 to 12 carbon atoms, $(CH_3)_3C-$,

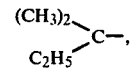

cyclohexyl or phenyl, $R^2$ represents an alkyl group containing from 1 to 4 carbon atoms and X represents chlorine, bromine or iodine.

2. A phosphonium halide according to claim 1 wherein $R^1$ is $(CH_3)_3C-$,

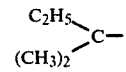

or a cyclohexyl group.

3. A phosphonium halide according to claim 1 wherein X is bromine.

4. A phosphonium halide according to claim 1 wherein $R^2$ is methyl.

5. A non-phytotoxic composition for combatting fungi, bacteria and mildew, said composition comprising an inert, non-phytotoxic diluent and an effective amount of a tris(aryl) alkyl phosphonium halide of the general formula

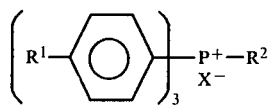

wherein $R^1$ represents an alkyl group containing from 6 to 12 carbon atoms, $(CH_3)_3C-$,

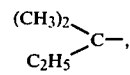

cyclohexyl or phenyl, $R^2$ represents an alkyl group containing from 1 to 4 carbon atoms and X represents chlorine, bromine or iodine.

6. A non-phytotoxic composition according to claim 5 wherein $R^1$ is $(CH_3)_3C-$,

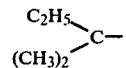

or a cyclohexyl group.

7. A non-phytotoxic composition according to claim 5 wherein X is bromine.

8. A non-phytotoxic composition according to claim 5 wherein $R^2$ is methyl.